United States Patent [19]
Nakagawa et al.

[11] Patent Number: 5,587,486
[45] Date of Patent: Dec. 24, 1996

[54] 1-AMINO-2-CYCLOHEXENE DERIVATIVE AND PRODUCTION PROCESS THEREFOR

[75] Inventors: Naoshi Nakagawa; Tadashi Hatanaka; Tatsuhiko Hayashibara; Manzo Shiono, all of Kurashiki, Japan

[73] Assignee: Kuraray Co., Ltd., Kurashiki, Japan

[21] Appl. No.: 497,086

[22] Filed: Jun. 30, 1995

[30] Foreign Application Priority Data

Jun. 30, 1994 [JP] Japan .................... 6-149597

[51] Int. Cl.$^6$ ................ C07D 209/56; C07D 333/50
[52] U.S. Cl. ............ 548/448; 548/441; 549/43; 549/57; 549/458; 549/471
[58] Field of Search .................. 548/448, 441; 549/43, 57, 458, 471

[56] References Cited

FOREIGN PATENT DOCUMENTS 0240107  10/1987  European Pat. Off. .

OTHER PUBLICATIONS

J. Chem. Soc., Chem. Commun., No. 21, pp. 1692–1693, 1989, S. V. Kessar, et al., "Photochemistry of Silylimines: Diels–Alder Trapping of a Photochemically Generated o-Quinodimethane Intermediate From o-(N-Trimethylsilyliminomethyl)Toluene".

Chemical Abstracts, vol. 111, No. 8, AN 69697k, 1989.

Beilstein Handbook of Organic Chemistry, vol. 17, Part 9, 4th Ed., p. 401 1979.

*Primary Examiner*—Jacqueline Haley
*Attorney, Agent, or Firm*—Oblon, Spivak, McClelland, Maier & Neustadt, P.C.

[57] ABSTRACT

1-amino-2-cyclohexene compounds represented by the following formula (I):

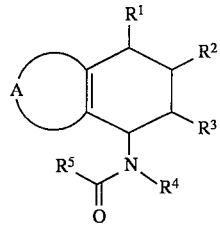

wherein the substituents are as defined in the specification, a process for preparing the compounds and their use as intermediates in the production of medicinal and agricultural agents is disclosed.

25 Claims, No Drawings

1-AMINO-2-CYCLOHEXENE DERIVATIVE AND PRODUCTION PROCESS THEREFOR

BACKGROUND OF THE INVENTION

1. Field of the Invention

The present invention relates to a 1-amino-2-cyclohexene derivative useful as an intermediate in the production of various medicines and agricultural agents and a production process therefor.

2. Discussion of the Background

Recently, condensed ring compounds containing hetero atoms (such as oxygen, nitrogen and sulfur) have been found to have various biological activities and vigorous developments have been made for them as medicines and agricultural agents. For example, Amemiya et al. have reported a dihydrobenzothiophene derivative or a tetrahydrobenzothiophene derivative having an inhibitory action on thromboxane synthetase (Journal of Medicinal Chemistry, 1989, vol. 32, pp. 1265–1272). Nagai et al. have reported a carbazole-3,4-dicarboximide derivative having anti-tumor activity (Japanese Patent Laid-Open No. 4-178387). Additionally, Dubroeucg et al. have reported a benzofuran or a benzothiophene carboxamide which has an effect as a tranquilizer, anti-anginal drug and immunomodulator (Japanese Patent Laid-open No. 63-39874).

Various studies have also been made for production processes for the condensed ring compounds. For condensed ring forming reactions, one method of bonding together the side chains of cyclic compounds having two side chains is the Robinson annelation. For example, Amemiya et al. obtain 4,5-dihydrobenzo[b]thiophene-6-carboxylic acid methyl ester by forming 7-oxo-4,5,6,7-tetrahydrobenzo[b]thiophene using 3-bromothiophene as a starting material (MacDowell et al., Journal of Heterocyclic Chemistry, 1965, vol. 2, pp. 44–48), methoxycarbonylating the same, reducing the ketone and then dehydrating with an acid. Further, in the method of Nagai et al., a carbazole skeleton is formed according to the Fisher indole synthesis using N-benzyl-4-oxocyclohexane-1,2-carboximide as the starting material and then reacting the same with phenylhydrazine. In Dubroeucg et al., 4-phenylbenzo[b]thiophene-6-carboxylic acid was obtained by condensing 3-benzoylpropionic acid and 2-thiophene carboxy aldehyde in the presence of acetic anhydride and potassium acetate to obtain 5-phenyl-3-(2-thienylmethylene)-2-furanone and heating the same in acetic acid in the presence of methane sulfonic acid. Kido et al. report a method of constructing the 2,4,5,6,7,7a-hexahydrobenzofuran-2-one skeleton by the condensation reaction of 2-methyl-3-vinylbutenolide and 2-formyl-6-methyl-5-heptenic acid methyl ester and then introducing the same to furoventalene having a benzofuran skeleton isolated from sea fan (*Gorgonia ventalina*) (Journal of Organic Chemistry, 1981, vol. 46, pp. 4264–4266).

As described above, condensed ring compounds are useful as intermediate products for the synthesis of various medicines and agricultural agents. However, there are few general production processes for condensed ring compounds, and the development of such general production processes is much in demand. The method described above of bonding side chains of cyclic compounds having two side chains with each other often requires multiple steps for the cyclizing reaction and, accordingly, functional groups that can be introduced may sometimes be restricted depending on the reaction conditions. In addition, the availability of starting materials significantly limits the applicability of such a process as a general process for producing the various desired condensed ring compounds.

On the other hand, cycloaddition reactions, typically represented by the Dieis-Alder reaction, have a feature capable of forming a condensed ring in a single stage since two bonds are formed in the same reaction. Examples include indole alkaloid synthesis by way of indole quinodimethane type diene (Magnus et al., Tetrahedron, 1981, vol, 37, pp. 3889–3897; Journal of American Chemical Society, 1982, vol. 104, pp. 1140–1141; Journal of American Chemical Society, 1983, vol. 105, pp. 4739–4749; Journal of American Chemical Society, 1983, vol. 105, pp. 4750–4757; Journal of American Chemical Society, 1984, vol. 106, pp. 2105–2114 and Accounts of Chemical Research, 1984, vol. 17, pp. 35–41), carbazole synthesis using pyrano[3,4-b]indol-3-one or pyrano[4,3-b]indol-3-one (Doren et al., Tetrahedron, 1989, vol. 45, pp. 6761–6770; Moody et al., Journal of Chemical Society, Perkin Transaction I, 1988, pp. 1407–1415; Journal of Chemical Society, Perkin Transaction I, 1989, pp. 376–377 and Journal of Chemical Society, Perkin Transaction I, 1990, pp. 673–679), and carbazole synthesis using vinyl indole (Pindur et al., Helvetica Chimica Acta, 1988, vol. 71, pp. 1060–1064; and Journal of Organic Chemistry, 1990, vol. 55, pp. 5368–5374).

Although the above-mentioned methods are excellent in being single stage condensed ring-forming reactions, the method of Magnus et al. is only used in the intramolecular Dieis-Alder reaction, while the method of using pyranoindol-3-one or vinyl indole requires multiple stages and/or special steps for the preparation of starting materials and further requires expensive starting materials and reagents. These methods thus cannot thoroughly take advantage of the single stage cyclization reaction from an industrial point of view. Further, each of the processes is applied only to carbazole derivatives, and thus cannot be said to be a general method for synthesizing condensed ring compounds.

SUMMARY OF THE INVENTION

Accordingly, one object of the present invention is to provide a novel intermediate product which can be used to make various condensed ring compounds.

Another object of the present invention is to provide a process for producing such intermediate products in a minimum number of steps and at a high yield taking advantage of the feature of the cycloaddition reaction, using easily available starting materials and without using expensive reagents.

These and other objects of the present invention have been satisfied by the discovery of 1-amino-2-cyclohexene derivatives and a production process therefor, wherein the 1-amino-2-cyclohexene derivatives are useful in the preparation of medicinal and agricultural agents.

DETAILED DESCRIPTION OF THE PREFERRED EMBODIMENTS

The present invention relates to a 1-amino-2-cyclohexene derivative represented by the following formula (I):

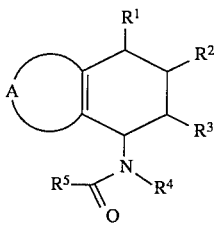

(I)

where A represents a bivalent organic group which may contain 1 to 3 oxygen atoms, nitrogen atoms and/or sulfur atoms, wherein A may form a ring having a total of 5–8 members, and the ring may form a condensed ring with one or more additional rings; $R^1$ represents a hydrogen atom, an alkyl group, an alkenyl group, an aryl group or an aralkyl group, $R^2$ represents a hydrogen atom, an alkyl group, an alkenyl group, an aryl group, an aralkyl group, a cyano group or a group represented by the formula: —$COR^{21}$, where $R^{21}$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, $R^3$ represents a cyano group, a nitro group or a group represented by the formula: —$COR^{31}$, where $R^{31}$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, $R^4$ represents an alkyl group, an alkenyl group, an aryl group or an aralkyl group, $R^5$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, in which $R^2$ and $R^{31}$ may join together to form a bivalent organic group optionally containing an oxygen atom or a nitrogen atom; and a process for producing a 1-amino-2-cyclohexene derivative (I) which comprises condensing an aldehyde represented by the formula (II):

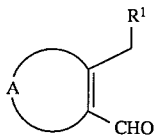

(II)

where A and $R^1$ are as defined above with a primary amine represented by the following formula (III):

$$H_2NR^4 \quad (III):$$

where $R^4$ is as defined above to obtain an imine represented by the following formula (IV):

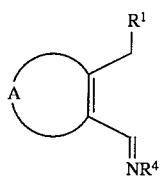

(IV)

where A, $R^1$ and $R^4$ are as defined above, and reacting the imine (IV) in the presence of a basic substance with a carbonylating agent represented by the following formula (V):

(V)

where $R^5$ is as defined above and X represents a leaving group, and an ethylene derivative represented by the following formula (VI):

(VI)

where $R^2$ and $R^3$ are as defined above, [hereinafter referred to as dienophile (VI)]; and a process for producing a 1,3-cyclohexadiene derivative represented by the following formula (IX):

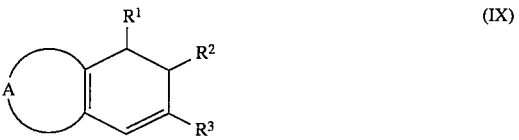

(IX)

where A, $R^1$, $R^2$ and $R^3$ are as defined above, which comprises subjecting the 1-amino-2-cyclohexene derivative (I) to an elimination reaction by a basic substance.

Examples of a ring formed by A include 5-membered rings such as a cyclopentene ring, a cyclopentadiene ring, a dihydrofuran ring, a furan ring, a pyrrole ring, a pyrroline ring, a dehydrodioxolane ring, a pyrazole ring, a pyrazoline ring, an imidazole ring, an oxazole ring, an isoxazole ring, a thiazole ring, an oxadiazole ring and a triazole ring; 6-membered rings such as a benzene ring, a cyclohexadiene ring, a cyclohexene ring, a pyran ring, a dihydropyran ring, a pyridine ring, a dihydropyridine ring, a tetrahydropyridine ring, a dehydrodioxan ring, a dehydromorpholine ring, a pyridazine ring, a dihydropyridazine ring, a tetrahydropyridazine ring, a pyrimidine ring, a dihydropyrimidine ring, a tetrahydropyrimidine ring, a pyrazine ring and a dihydropyrazine ring; 7-membered rings such as a cycloheptatriene ring, a cycloheptadiene ring, a cycloheptene ring, as well as aza, oxa or thia substituted derivatives thereof, and a thiazepin ring; and 8-membered rings such as a cyclooctatetraene ring, a cyclooctatriene ring, a cyclooctadiene ring, a cyclooctene ring as well as aza, oxa or thia substituted derivatives thereof.

Where the ring formed by A forms a condensed ring with one or more other rings, A can include a benzofuran ring, an isobenzofuran ring, a chromene ring, an indolizine ring, an isoindole ring, an indole ring, a quinolizine ring, an indazole ring, an isoquinoline ring, a quinoline ring, a phthalazine ring, a naphthyridine ring, a quinoxaline ring, a quinazoline ring, a benzothiophene ring and the hydrogenated forms thereof. Any of the above rings may have a substituent.

In the present invention, "alkyl" includes linear or branched alkyl groups of 1 to 8 carbon atoms such as methyl, ethyl, propyl, isopropyl, butyl, isobutyl, sec-butyl, tertbutyl, pentyl, isopentyl, neopentyl, hexyl, heptyl and octyl; and cycloalkyl groups such as cyclopropyl, cyclobutyl, cyclopentyl and cyclohexyl. "Alkenyl" includes vinyl, allyl, methallyl, butenyl, plenyl and octenyl.

"Aryl" includes phenyl or naphthyl, either of which may have a substituent. Specific examples include phenyl, naphthyl, fluorophenyl, chlorophenyl, bromophenyl, methoxyphenyl, nitrophenyl, tolyl, xylyl and isopropylphenyl. "Aralkyl" includes benzyl which may have a substituent, such as benzyl, methoxybenzyl, dimethoxybenzyl, nitrobenzyl, chlorobenzyl and bromobenzyl.

"Alkoxy" includes linear or branched alkoxy groups of 1 to 8 carbon atoms, such as methoxy, ethoxy, propoxy, isopropoxy, butoxy, hexyloxy and octyloxy; and cycloalkyloxy groups such as cyclopentyloxy and cyclohexyloxy. "Alkenyloxy" includes alkenyloxy groups of 1 to 8 carbon atoms such as allyloxy, methallyloxy, plenyloxy and octenyloxy.

"Aryloxy" includes phenoxy which may have a substituent, such as phenoxy, methylphenoxy, methoxyphenoxy, chlorophenoxy, bromophenoxy and nitrophenoxy. "Aralkyloxy" includes benzyloxy which may have a substituent, such as benzyloxy, chlorobenzyloxy, bromobenzyloxy, methoxybenzyloxy, methylbenzyloxy and nitrobenzyloxy. "Amino group having a substituent" includes secondary amino groups substituted with aralkyl, alkylene, aryl and/or aralkyl, such as dimethylamino, diethylamino, N-phenylmethylamino, N-benzylmethylamino and 1-pyrrolidyl.

The leaving group represented by X in the general formula (V) includes halogen, such as chlorine and bromine; and acyloxy, such as acetoxy, propionyloxy, butylyloxy and valeryloxy.

As an example of 1-amino-2-cyclohexene derivative (I), there can be mentioned a tetrahydrobenzothiophene derivative or a tetrahydrobenzofuran derivative represented by the following general formula (I-1):

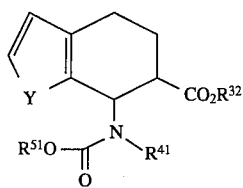

(I-1)

where each of $R^{32}$, $R^{41}$ and $R^{51}$ represents an alkyl group, an aryl group or an aralkyl group and Y represents a sulfur atom or an oxygen atom, and a tetrahydrocarbazole derivative represented by the following general formula (I-2):

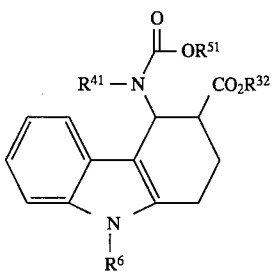

(I-2)

(where $R^{32}$, $R^{41}$ and $R^{51}$ are as defined above, and $R^6$ represents an alkyl group, an aralkyl group, an acyl group, an alkoxycarbonyl group, an alkanesulfonyl group or an arenesulfonyl group).

Examples of the aldehyde (II) include a 3-methylthiophene-2-aldehyde or a 3-methylfuran-2-aldehyde represented by the following formula (VII):

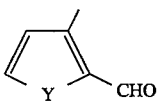

Z(VII)

where Y is as defined above, or 2-methylindole-3-aldehyde represented by the following formula (VIII):

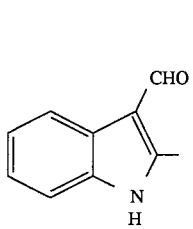

(VIII)

Examples of the 1,3-cyclohexadiene derivative (IX) include a dihydrobenzothiophene carboxylic acid derivative or a dihydrobenzofuran carboxylic acid derivative represented by the following general formula (IX-11):

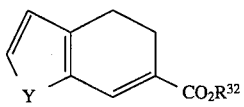

(IX-11)

where $R^{32}$ and Y are as defined above, or a dihydrocarbazol carboxylic acid derivative represented by the following general formula (IX-21):

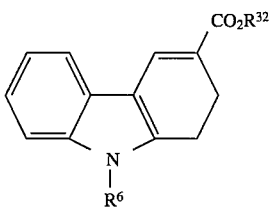

(IX-21)

where $R^{32}$ and $R^6$ are as defined above.

Compound (IX-11) and compound (IX-21) can be transformed, if necessary, by subjecting them to hydrolysis to obtain a dihydrobenzothiophene carboxylic acid derivative or a dihydrobenzofuran carboxylic acid derivative represented by the following general formula (IX-1):

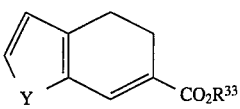

(IX-1)

where Y is as defined above and $R^{33}$ represents a hydrogen atom, an alkyl group, an aryl group or an aralkyl group, or a dihydrocarbazol carboxylic acid derivative represented by the following general formula (IX-2):

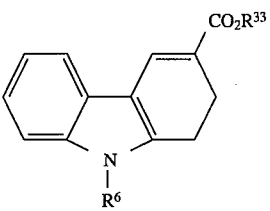

(IX-2)

where $R^{33}$ and $R^6$ are as defined above, respectively.

In compounds (I-2), (IX-2) and (IX-21), $R^6$ is preferably a group used conventionally as a protecting group for nitrogen in indole. More specifically, the alkyl groups and aralkyl groups which may be used are those described previously. The acyl groups include alkanoyl groups which may have a substituent, such as formyl, acetyl, propionyl, butyryl, isobutyryl, valeryl, isovaleryl, pivaloyl, chloroacetyl and trifluoroacetyl; and benzoyl or naphthoyl groups which may have a substituent, such as benzoyl, methoxybenzoyl, chlorobenzoyl and naphthoyl. The alkoxycarbonyl groups of $R^6$ include lower alkoxycarbonyl groups such as methoxycarbonyl, ethoxycarbonyl, propoxycarbonyl, isopropoxycarbonyl, butoxycarbonyl and tert-butoxycarbonyl; aryloxycarbonyl groups which may have a substituent, such as phenoxycarbonyl and nitrophenoxycarbonyl; and aralkyloxycarbonyl groups which may have a substituent, such as benzyloxycarbonyl and methoxybenzyloxycarbonyl. The alkane sulfonyl groups of $R^6$ include methane sulfonyl and ethane sulfonyl. The arene sulfonyl groups of $R^6$ include benzene sulfonyl, toluene sulfonyl and bromobenzene sulfonyl.

Conversion from the aldehyde (II) to the imine (IV) is conducted by condensing the aldehyde (II) with the amine (III). The reaction can be conducted under conventional conditions used generally for obtaining an imine from an aldehyde and a primary amine. For example, the conversion can be conducted by mixing the aldehyde (II) and the amine (III) in the presence or absence of a solvent. Suitable solvents are those which give no undesired effect on the reaction, including aliphatic hydrocarbon solvents such as pentane, hexane, heptane and ligroin; aromatic hydrocarbon solvents such as benzene, toluene, xylene and chlorobenzene; ether solvents such as diethyl ether, tetrahydrofuran and dioxane; alcohol solvents such as methanol and ethanol; ester solvents such as methyl acetate, ethyl acetate and butyl acetate; or a mixture thereof, and reacting in the presence or absence of a dehydrating agent, such as silica gel, molecular sieves, alumina, sodium sulfate, magnesium sulfate and copper sulfate.

Further, reaction may also be conducted in an azeotropic solvent with water while removing water by azeotropic distillation.

Isolation and purification from a reaction mixture of the thus obtained imine (IV) is conducted using conventional techniques. For instance, the imine (IV) can be obtained by separating insoluble matter contained in the reaction mixture by filtration, condensing the liquid filtrate, recrystallizing residues and then purifying, for example, by chromatography. Further, crude products can be used as they are obtained, without purification, in the succeeding reaction. When the resultant imine (IV) is deposited from the reaction mixture, it is recovered by filtration and purified if necessary, by recrystallization and then can be used in a succeeding reaction.

Conversion from the imine (IV) to the 1-amino-2-cyclohexene derivative (I) is conducted in the presence of a basic substance by reacting imine (IV) with carbonylating agent (V) and dienophile (VI). As the carbonylating agent used herein, there can be mentioned carboxylic acid anhydrides, such as acetic anhydride, propionic anhydride, butyric anhydride, valeric anhydride and trifluoro acetic anhydride; carboxylic acid halides, such as acetyl chloride, propionyl chloride, butyryl chloride, isobutyryl chloride, valeryl chloride, isovaleryl chloride, pivaroyl chloride and benzoyl chloride; chloroformate esters, such as methyl chloroformate, ethyl chloroformate, propyl chloroformate, isopropyl chloroformate, butyl chloroformate, allyl chloroformate, phenyl chloroformate, nitrophenyl chloroformate and benzyl chloroformate; carbamic acid halides, such as N,N-dimethyl carbamic acid chloride. Among these, chloroformate esters are preferred. The amount of the carbonylating agent (V), while different depending on the type used, ranges from 0.5 to 20 mol, preferably, from 1.1 to 10 mol based on one mol of the imine (IV).

As the dienophile (VI), there can be mentioned acrylates which may have a substituent, acrylamides which may have a substituent, acrylonitrile which may have a substituent, propenal which may have a substitutent, vinyl ketones which may have a substituent, maleic acid esters, maleic anhydride, maleimides, fumaric acid esters, fumaronitrile and nitroethylene which may have a substituent. More specific examples include alkyl acrylates such as methyl acrylate, ethyl acrylate, propyl acrylate, isopropyl acrylate, butyl acrylate, isobutyl acrylate, sec-butyl acrylate, tert-butyl acrylate, pentyl acrylate, hexyl acrylate, cyclopentyl acrylate and cyclohexyl acrylate; aryl acrylates, such as phenyl acrylate, naphthyl acrylate, chlorophenyl acrylate, bromophenyl acrylate, methoxyphenyl acrylate, nitrophenyl acrylate, tolyl acrylate, xylyl acrylate and isopropylphenyl acrylate; aralkyl acrylates, such as benzyl acrylate, methoxybenzyl acrylate, dimethoxybenzyl acrylate, nitrobenzyl acrylate, chlorobenzyl acrylate and bromobenzyl acrylate; substituted acrylates, such as methyl crotonate and methyl succinate; N-substituted acrylamides, such as N,N-dimethylacrylamide; substituted acrylamides, such as N,N-dimethylcrotonamide and N,N-dimethylcinnamamide; acrylonitrile; aromatic-substituted acrylonitriles, such as crotononitrile and cinnamonitrile; acrolein; substituted propenals, such as crotonaldehyde and cinnamaldehyde; vinyl ketones, such as methyl vinyl ketone, ethyl vinyl ketone, phenyl vinyl ketone, styryl methyl ketone, 3-penten-2-one and 1-penten-3-one; maleates, such as dimethyl maleate; maleic anhydride; fumarates, such as dimethyl fumarate; maleimides, such as N-phenyl maleimide; fumaronitrile and vinyl nitro compounds such as nitroethylene. The amount of dienophile (VI) used ranges from 0.5 to 50 mol, preferably from 1.1 to 10 mol, based on 1 mol of the imide (IV).

The basic substance used for the reaction includes tertiary amines such as trimethyl amine, triethyl amine, tributyl amine, trihexyl amine, trioctyl amine, diisopropyl ethyl amine, dimethyl aniline, diethyl aniline and N-methylmorpholine; alkali metal carbonates, such as lithium carbonate, sodium carbonate and potassium carbonate; alkali metal hydroxides, such as lithium hydroxide, sodium hydroxide and potassium hydroxide; alkaline earth metal hydroxides, such as magnesium hydroxide and calcium hydroxide; and metal hydrides, such as a lithium hydride and sodium hydride. Among these, a sterically hindered (i.e. bulky) tertiary amine which exhibits relatively high basicity and is soluble in the reaction system, such as diisopropyl ethyl amine, is preferred. The amount of the basic substance used ranges from 0.5 to 50 mol, preferably from 1.1 to 10 mol, based on one mol of the imine (IV). The amount is preferred to be more than 1 mol per 1 mol of the carbonylating agent (V) used.

The conversion reaction from imine (IV) to 1-amino-2-cyclohexene derivative (I) can be conducted with or without solvent. When the reaction is conducted in a solvent, there is no particular restriction on the solvent to be used so long as it does not give any undesired effect on the reaction. Suitable solvents include aromatic hydrocarbon solvents, such as benzene, toluene, xylene, chlorobenzene, trimethylbenzene and cumene. The amount of the solvent used preferably ranges from 3 to 200 times by weight based on the imine (IV).

The reaction temperature may vary depending on the solvent, the carbonylating agent (V) and the dienophile (VI) used and is preferably within a range from 40° C. to the reflux temperature for the reaction system. The reaction time, which may vary depending on the reaction temperature, preferably ranges from 30 minutes to 24 hours. By properly controlling the reaction temperature, the reaction time can be controlled.

The conversion reaction described above can be practiced, for example, as shown below. Dienophile (VI) and the basic substance are added to the solution of imine (IV), and carbonylating agent (V) is added to the resultant mixture within a temperature range from under ice cooling (0° C.) to the reflux temperature of the reaction mixture. After the completion of the addition, the mixture is heated to the desired temperature until imine (IV) disappears.

Isolation and purification of the thus obtained 1-amino-2-cyclohexene derivative (I) from the mixture is conducted using conventional organic purification methods. For instance, after cooling the reaction mixture to a room temperature, it is washed with an aqueous solution of sodium hydrogen carbonate and saline water, dried on sodium sulfate and the solvent is then distilled off to obtain a crude product.

Conversion from 1-amino-2-cyclohexene derivative (I) to 1,3-cyclohexadiene derivative (IX) is conducted in the presence of a basic substance by subjecting 1-amino-2-cyclohexene derivative (I) to an elimination reaction.

The basic substance used for the elimination reaction is not particularly limited so long as the substance does not cause side reaction and has sufficient basicity to cause elimination to form the 1,3-cyclohexadiene derivative (IX). Suitable basic substances include metal alkoxides, such as lithium methoxide, sodium methoxide, potassium methoxide, sodium ethoxide, potassium ethoxide, potassium tert-butoxide and sodium tert-amyloxide; metal amides, such as lithium amide, sodium amide, potassium amide, lithium diisopropyl amide, lithium cyclohexyl isopropyl amide, lithium hexamethyl disilazide, sodium hexamethyl disilazide, potassium hexamethyl disilazide and lithium tetramethyl piperizide; amines, such as diazabicyclo[2.2.2]octane (DABCO) and diazabicycle[5.4.0]undec-7-ene (DBU); and quaternary ammonium hydroxides, such as trimethyl benzyl ammonium hydroxide, and tributyl ammonium hydroxide. In the case of quarternary ammonium hydroxides, the quaternary ammonium hydroxide can be formed in the system from a corresponding halide and an alkali metal hydroxide. The amount of the basic substance used ranges from 0.8 to 20 mol, preferably from 0.95 to 10 mol, based on one mol of the 1-amino-2-cyclohexene derivative (I).

The elimination reaction is usually conducted in a solvent and the solvent used varies depending on the basic substance used. Suitable solvents include alcohol solvents, such as methanol, ethanol, propanol, isopropyl alcohol and tert-butyl alcohol; ether solvents, such as diethyl ether, tetrahydrofuran, dioxane and 1,2-dimethoxy ethane; polar aprotic solvents, such as N,N-dimethylformamide and dimethyl sulfoxide; hydrocarbon solvents, such as hexane, heptane, cyclohexane, petroleum ether and ligroin; aromatic hydrocarbon solvents, such as benzene, toluene and xylene; water; or a mixture thereof. The amount of the solvent used preferably ranges from 3 to 200 times by weight based on 1-amino-2-cyclohexene derivative (I).

The reaction temperature for the elimination reaction, while different depending on the basic substance and the solvent used, preferably ranges from 0° C. to 150° C. The reaction temperature varies depending on the reaction temperature and preferably ranges from 30 minutes to 24 hours.

Isolation and separation of the thus obtained 1,3-cyclohexadiene derivative (IX) from the reaction mixture can be performed using conventional organic methods. For instance, 1,3-cyclohexadiene derivative (IX) can be obtained by adding the reaction mixture to iced water, separating an organic layer, then extracting an aqueous layer with an organic solvents, such as ethyl acetate, diethyl ether, dichloromethane or toluene, collecting the organic layer and washing with an aqueous sodium chloride solution, drying over sodium sulfate or magnesium sulfate and then concentrating to obtain a crude product, which is purified, for example, by recrystallization and/or chromatography. Further, it is possible to use the crude products as they are obtained, with no further purification, in the succeeding reaction or use the reaction mixture without isolation or purification in the succeeding reaction.

The 1,3-cyclohexadiene derivative (IX) in which $R^3$ represents a group represented by the formula —$COR^{31}$, and $R^{31}$ represents an alkoxy group, an alkenyloxy group, an aryloxy group or an aralkyloxy group, can be converted by hydrolysis into a 1,3-cyclohexadiene carboxylic acid derivative represented by the following general formula (IX-3):

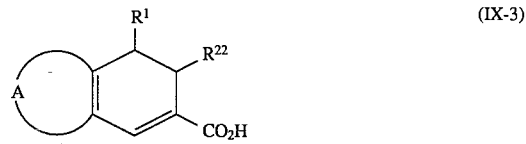

where A and $R^1$ are as defined above, $R^{22}$ represents $R^2$ or carboxyl group, and $R^2$ is as defined above. The carboxylic acid (IX-3) is a compound included in the 1,3-cyclohexadiene derivative (IX).

The hydrolysis reaction can be conducted in accordance with a conventional method used to convert an ester to a corresponding carboxylic acid. For instance, it can be conducted by adding an aqueous solution containing a sufficient amount of an alkali metal hydroxide for hydrolysis to the 1,3-cyclohexadiene derivative (IX) in which the group represented by $R^3$ is an alkoxy carbonyl group, an alkenyloxy carbonyl group, an aryloxy carbonyl group and an aralkyloxy carbonyl group, or a solution thereof, and stirring at a temperature within a range from 0° C. to 100° C. till the 1,3-cyclohexadiene derivative (IX) in which the group represented by $R^3$ is an alkoxy carbonyl group, an alkenyloxy carbonyl group, an aryloxy carbonyl group, an aralkyloxy carbonyl group disappears completely.

Isolation and purification of the thus obtained carboxylic acid (IX-3) from the reaction mixture can be conducted using conventional organic techniques. For instance, a crude product is obtained by distilling off low boiling ingredients of the reaction mixture, adding water as necessary to the resultant residue, extracting the same with an organic solvent such as ethyl acetate, diethyl ether, dichloromethane or toluene, rendering the aqueous layer acidic, with, for example, hydrochloric acid, then extracting with an organic solvent such as ethyl acetate, diethyl ether or dichloromethane, washing the liquid extract with an aqueous sodium chloride solution, then drying by using sodium sulfate or the like and distilling off the solvent. The crude product is then purified, for example, by chromatography or recrystallization to obtain the carboxylic acid (IX-3).

The thus obtained carboxylic acid (IX-3) can be converted into the 1,3-cyclohexadiene derivative (IX) by esterification under conventional conditions.

Among the 1,3-cyclohexadiene derivatives (IX), the compound represented by the following formula (IX-12):

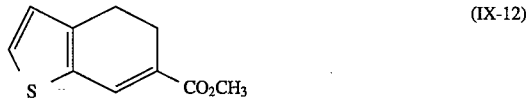

can be converted into 2-(1-imidazolylmethyl)-4,5-dihydrothianaphthene-6-carboxylic acid, which has an inhibitory action on thromboxane synthetase and is useful in pharmaceuticals in accordance with a method as described in Journal of Medicinal Chemistry, 1989, vol. 32, pp. 1265–1272. Further, the compound represented by the following general formula (IX-13):

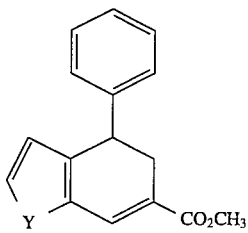

where Y is as defined above, can be converted by dehydrogenation, hydrolysis and amidation by sec-butylamine and N-methylation into N-sec-butyl-N-methyl-5-phenylbenzo[b]furan-6-carboxamide or N-sec-butyl-N-methyl-5phenyl-benzo-[b]thiophene-6-carboxamide having an activity as a tranquilizer, anti-anginal drug and immunomodulator. Further, the compound represented by the following formula (IX-14):

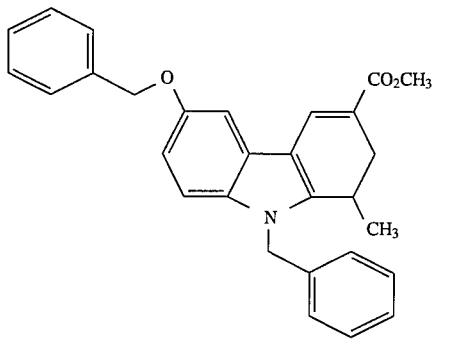

can be converted by conjugate addition of cyanide ion, hydrolysis, imidation, debenzylation and dehydrogenation into N-(N-dimethylaminoethyl)-8-hydroxy-1-methyl-9H-carbazol-3,4-dicarboximide having anti-tumor activity.

The aldehyde (II) can be obtained, for example, by formylating the compound represented by the following general formula (X):

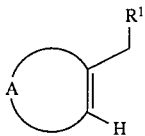

where A and $R^1$ are as defined above. For instance, 3-methylthiophene-2-aldehyde can be obtained from 3-methylthiophene, 3-methylfuran-2-aldehyde can be obtained from 3-methylfuran and 2-methylindole-3-aldehyde can be obtained from 2-methylindole by formylation using Vilsmeier's reagent (N,N-dimethylformamide-phosphoroxy chloride), respectively, and the aldehydes are available as commercial products.

Having generally described this invention, a further understanding can be obtained by reference to certain specific examples which are provided herein for purposes of illustration only and are not intended to be limiting unless otherwise specified.

EXAMPLES

Example 1

3-methylthiophene-2-aldehyde (103 g, 0.816 mol) was mixed with hexane (100 ml), to which aniline (74.4 ml, 0.816 mol) was added and stirred at room temperature for 7 hours. After separating deposited crystalline solids by filtration, and washing with hexane, 139.5 g (yield: 85%) of 3-methylthiophene-2-aldehyde phenylimine was obtained. After concentrating the liquid filtrate and stirring at room temperature for a further 12 hours, 7.30 g (yield: 4%) of 3-methylthiophene-2-aldehyde phenylimine was obtained by post treatment in the same manner as above. $^1$H-NMR spectra (chemical shift, ppm: in CDCl$_3$); 2.47 (3H, s), 6.92 (1H, d, J=4.9 Hz), 7.15–7.30 (3H), 7.30–7.45 (3H), 8.61 (1H).

3-methylthiophene-2-aldehyde phenylimine (50 g, 0.248 mol), methyl acrylate (224 ml, 2.48 mol) and diisopropyl ethylamine (173 ml, 0.993 mol) were mixed in xylene (1000 ml) and stirred under ice cooling. Methyl chloroformate (76.8 ml, 0.993 mol) was added to the mixture. After completing the addition, the reaction mixture was heated under reflux for 3 hours and then allowed to cool to room temperature. The reaction mixture was washed with an aqueous solution of sodium hydrogen carbonate and an aqueous solution of sodium chloride and dried over sodium sulfate. After distilling off the solvent, 83 g of crude N-methoxycarbonyl-N-phenyl-7-amino-4,5,6,7-tetrahydrobenzo[b]thiophene-6-carboxylic acid methyl ester was obtained.

The thus obtained crude N-methoxycarbonyl-N-phenyl-7-amino-4,5,6,7-tetrahydrobenzo[b]thiophene-6-carboxylic acid methyl ester (83 g) was dissolved in methanol (830 ml), sodium methoxide (95.8 g in 28% methanol solution) was added and stirred at 60° C. for 2 hours and then allowed to cool to room temperature. Water (500 ml) and potassium hydroxide (27.9 g) were added to the reaction mixture and stirred at 60° C. for one hour. After distilling off methanol, water was added to the residue and extracted with toluene. The resultant aqueous layer was rendered acidic with dilute hydrochloric acid and extracted with ethyl acetate. The liquid extract was washed with an aqueous solution of sodium chloride and then dried over sodium sulfate. The solvent was distilled off and the resultant residue was purified by recrystallization (in methyl acetate/hexane) to obtain 30.9 g (yield: 72.3% from phenylimine) of 4,5-dihydrobenzo[b]thiophene-6-carboxylic acid as a pale yellow crystalline powder. By concentrating and then recrystallizing the filtrate, 4.3 g (yield: 10.1%) of second crystals were obtained. Melting point: 151.5°–153° C. $^1$H-NMR spectra (chemical shift, ppm: in CDCl$_3$): 2.70 (2H, m), 2.88 (2H, m), 6.93 (1H, d, J=4.9 Hz), 7.37 (1H, d, J=4.9 Hz), 7.66 (1H, s). Conditions for high speed liquid chromatographic analysis:

Column: Hiber LiCrospher 100 RP-18 (5 μm) 250 mm×4 mm φ (manufactured by Cica-MERCK)

Eluent: methanol/water (volume ratio 1:1) 0.9 ml/min

Column temperature: 45° C.

Detector: UV absorption detector

Wavelength: 254 nm

Retention time: 6.1 min

Purity (surface area percentage): 99.6%

Example 2

3-methylthiophene-2-aldehyde phenylimine (1.92 kg, 9.48 mol), diisopropyl ethyl amine (4.96 kg, 38.34 mol), methyl acrylate (4.13 kg, 47.94 mol) and methyl chloroformate (3.63 kg, 38.4 mol) were mixed in xylene (30 liter) at room temperature and stirred at 80°–100° C. under reflux for 3 hours. After cooling to room temperature, sodium hydrogen carbonate (10% aqueous solution, 10 liter) and water (7 liter) were added. After washing the organic layer with sodium chloride (20% aqueous solution), N-methoxycarbonyl-N-phenyl-7-amino-4,5,6,7-tetrahydrobenzo[b]thiophene-6-carboxyl acid methyl ester was obtained by filtration as crystalline solids (660 g, yield: 20% from imine). $^1$H-NMR spectra (chemical shift, ppm: in CDCl$_3$): 0.95–1.23, 1.65–1.85 (joined 1H, m), 1.85–2.25 (1H, m), 2.25–2.75 (2H, m), 2.75–3.20 (1H, m), 3.50–4.00 (1H, br), 3.71 (3H, s), 3.82 (3H, s), 6.85–7.40 (joined 1H, m), 6.60–6.95 (2H, m), 6.95–7.60 (4H, m).

nyl-N-phenyl-4,5,6,7tetrahydrobenzo[b]thiophene-6-carboxylic acid methyl ester.

| Example No. | Basic Substance | | Imine-based equivalent of methyl chloroformate | Reaction time (Hr) | HPLC area ratio (%) | | | |
|---|---|---|---|---|---|---|---|---|
| | Compound | Imine-based equivalent | | | Imine | Aldehyde | Carbamate | Tetrahydrobenzothiophene |
| 5 | NaOH | 4 | 2 | 0.5 | 0 | 31 | 14 | 54 |
| 6 | Na$_2$CO$_3$ | 4 | 2 | 5 | 0 | 16 | 6 | 78 |
| 7 | K$_2$CO$_3$ | 5 | 4 | 0.5 | 0 | 41 | 15 | 44 |
| 8 | K$_2$CO$_3$ | 10 | 2 | 0.2 | 0 | 60 | 20 | 20 |
| 9 | LiH | 4 | 2 | 1.5 | 0 | 27 | 11 | 62 |

Example 3

N-methoxycarbonyl-N-phenyl-7-amino-4,5,6,7-tetrahydrobenzo[b]thiophene-6-carboxylic acid methyl ester (100 mg, 0.290 mmol) was dissolved in methanol (3 ml), to which sodium methoxide (28% methanol solution, 1 ml) was added and stirred at room temperature overnight. The reaction mixture was poured into ice water and extracted with diethyl ether. After washing the liquid extract with an aqueous solution of sodium chloride and drying over sodium sulfate, the solvent was distilled off. The residue was purified by silica gel column chromatography to obtain 46.7 mg (yield 48%) of 4,5-dihydrobenzo[b]thiophene-6-carboxylic acid methyl ester as white crystalline solids. $^1$H-NMR spectra (chemical shift, ppm: in CDCl$_3$): 2.68 (2H, m), 2.84 (2H, m), 3.79 (3H, s), 6.90 (1H, d, J=4.9 Hz), 7.31 (1H, d, J=4.9 Hz), 7.53 (1H, s).

Example 4

4,5-dihydrobenzo[b]thiophene-6-carboxylic acid methyl ester (100 mg, 0.515 mmol) was dissolved in methanol (5 ml), to which potassium hydroxide (1N aqueous solution, 2 ml) was added and stirred under heating and reflux for 3 hours. After allowing the reaction mixture to cool, the methanol was distilled off. The resultant mixture was diluted with water and extracted with toluene. The aqueous layer was rendered acidic by using 1N hydrochloric acid and extracted with ethyl acetate. After washing the liquid extract with an aqueous solution of sodium chloride and drying it over sodium sulfate, the solvent was distilled off. 76 mg (yield: 82%) of 4,5-dihydro[b]thiophene-6-carboxylic acid showing the same physical property values as those obtained in Example 1 was obtained as crystalline solids by recrystallizing the residue (in methyl acetate/hexane).

Examples 5–9

Table 1 shows results of analysis by high speed chromatography when reaction was conducted in the same manner as in Example 2 using various basic substances. In the table, imine represents 3-methylthiophen-2-aldehyde phenylimine, aldehyde represents 3-methylthiophene-2-aldehyde, carbamate represents methyl N-phenyl carbamates, and tetrahydrobenzothiophene represents N-methoxycarbonyl-N-phenyl-7-amino-4,5,6,7-tetrahydrobenzo[b]thiophene-6-carboxylic acid methyl ester.

Condition for high speed liquid chromatographic analysis:
Column: Hiber LiCrosorb Si-60 (5 μm) 250 mm×4 mm φ (manufactured by Cica-MERCK)
Column temperature: 32° C.
Eluent: hexane/tetrahydrofuran (volume ratio 10:1) 1 ml/min
Detector: UV absorption detector
Wavelength: 254 nm

Example 10

3-methylthiophene-2-aldehyde phenylimine (100 mg, 0.497 mmol) and triethylamine (0.21 ml, 1.49 mmol) were mixed in xylene, to which acetyl chloride (0.14 ml, 1.99 mmol) was added under ice cooling. Methyl acrylate (0.22 ml, 2.48 mmol) was added to the resultant mixture and stirred under reflux for 7 hours. After allowing the reaction mixture to cool, water was added and the mixture was extracted with ethyl acetate. After washing the liquid extract with an aqueous solution of sodium chloride and drying over sodium sulfate, the solvent was distilled off to obtain 300 mg of crude products. Purification by silica gel column chromatography gave 114 mg (yield: 83%) of N-acetyl-N-phenyl-7-amino-4,5,6,7-tetrahydrobenzo[b]thiophene-6-carboxylic acid methyl ester. $^1$H-NMR spectra (chemical shift, ppm: in CDCl$_3$): 1.00–1.50 (1H, m), 1.73, 1.86 (joined 3H, s×2), 1.85–2.20 (1H, m), 230–2.85 (2.5H), 2.95–3.20 (0.5H, m), 3.74, 3.82 (joined 3H, s×2), 6.63–6.85 (2H), 7.15–7.70 (5H).

Example 11

N-acetyl-N-phenyl-7-amino-4,5,6,7-benzo[b]thiophene-6-carboxylic acid methyl ester (134 mg, 0.407 mmol) was dissolved in methanol (5 ml), to which sodium methoxide (28% methanol solution; 157 mg, 0.813 mmol) was added and stirred at room temperature. Sodium methoxide (28% methanol solution, 0.16 ml) was then added at 4 hr, 10 hr, and 28.5 hr, respectively, and they were stirred for 35.5 hours at room temperature. After heating the reaction mixture for 45 minutes under reflux, it was allowed to cool to room temperature. The reaction mixture was poured into ice water and extracted with diethyl ether. After washing the liquid extract with an aqueous solution of sodium chloride and drying over sodium sulfate, the solvent was distilled off to obtain 250 mg of crude products. They were purified by silica gel column chromatography to obtain 66 mg (yield: 84%) of 4,5-dihydrobenzo[b]thiophene-6-carboxylic acid methyl ester showing the same physical property values as those obtained in Example 3.

Example 12

2-methylindole-3-carboxaldehyde (10 g, 0.06 mol) was mixed with hexane (40 ml), to which aniline (9.6 ml, 0.11 mol) was added and stirred at 70° C. for 3.5 hours under reflux. Then, toluene (20 ml) was added and dissolved. The mixture was then submitted to silica gel column chromatography. The column was eluted by a developing solvent of hexane/ethyl acetate=3/1 and a fraction containing the desired product was concentrated by distilling off the solvent, to obtain 10.5 g (yield: 75%) of 2-methylindole-3-carboxaldehyde imine. $^1$H-NMR spectra (chemical shift, ppm: in $CDCl_3$): 2.63 (3H, s), 7.15–7.42 (8H, m), 8.19 (1H, s), 8.45–8.48 (1H, m), 8.69 (1H, s).

2-methylindole-3-carboxaldehyde imine (100 mg, 4.5 mmol), methyl acrylate (0.194 g, 22.5 mmol) and diisopropyl ethyl amine (0.116 g, 9.0 mmol) were mixed in toluene (2 ml) and stirred at 80° C. Ethyl chloroformate (0.098 g, 9.0 mmol) was added to the mixture. After completing the addition, the reaction mixture was heated for one hour under reflux and allowed to cool to room temperature. Water was added and the mixture was extracted with toluene. The organic layer was washed with an aqueous solution of sodium chloride and dried over sodium sulfate. The solvent was distilled off to obtain crude products of N, 9-bis(ethoxycarbonyl)-N-phenyl-1-amino- 1,2,3,4-tetrahydro-9H-carbazole-2-carboxylic acid methyl ester. Silica gel column chromatography using a developing solvent of hexane/ethyl acetate=5/1, gave a fraction containing the desired product. The product was concentrated by distilling off the solvent, to obtain 150 mg (yield: 71.8% from imine) of N,9-bis(ethoxycarbonyl)-N-phenyl-1-amino-1,2,3,4-tetrahydro-9H-carbazole-3-carboxylic acid methyl ester. $^1$H-NMR spectra (chemical shift, ppm: in $CDCl_3$): 1.15–1.25 (3H, m), 1.40–1.51 (3H, m), 1.88–2.19 (2H, m), 2.68–2.91 (2H, m), 2.95–3.11 (1H, m), 3.75 (3H, s), 4.15–4.32 (2H, m), 4.40–4.51 (2H, m), 6.25–6.35 (1H, d, J=7.9 Hz), 6.75–6.88 (2H, m), 7.10–7.20 (2H, m), 7.22–7.38 (2H, m), 7.59–7.60 (1H, m), 8.10–8.20 (1H, m).

The thus obtained N,9-bis(ethoxycarbonyl-N-phenyl-1-amino-1,2,3,4-tetrahydro-9H-carbazole-3-carboxylic acid methyl ester was dissolved in methanol (10 ml), to which sodium methoxide (1 g in 28% methanol solution) was added. After stirring at room temperature for 2 hours, water was added to the reaction mixture and methanol was distilled off. Water was then added to the residue, which was extracted with ethyl acetate. After washing the liquid extract with an aqueous solution of sodium chloride, it was dried over sodium sulfate. The solvent was distilled off and the residue was submitted to silica gel column chromatography, eluting with a developing solvent of hexane/ethyl acetate= 5/1. A fraction containing the desired product was concentrated by distilling off the solvent, to obtain 80 mg (yield: 59.7% from imine) of 9-ethoxycarbonyl-1,2-dihydro-9H-carbazole-3-carboxylic acid methyl ester. $^1$H-NMR spectra (chemical shift, ppm: in $CDCl_3$): 1.12–1.35 (3H, m), 2.43–2.68 (3H, m), 2.79–2.90 (1H, m), 3.75 (3H, s), 4.18–4.31 (2H, m), 6.77–6.89 (2H, m), 7.25–7.35 (1H, m), 7.58–7.65 (1H, d, J=6.7 Hz), 7.77 (1H, s).

Example 13

3-methylthiophene-2-aldehydimine (1 g, 5 mmol), dimethyl malonate (3.6 g, 25 mmol) and diisopropyl ethyl amine (1.28 g, 10 mmol) were mixed in toluene (4 ml) and stirred at 80° C.. Ethyl chloroformate (1.07 g, 10 mmol) was added to the mixture. After completing the addition, the reaction mixture was heated for one hour under reflux and allowed to cool to room temperature. Water was added and the mixture was extracted with toluene. The organic layer was washed with an aqueous solution of sodium chloride and dried over sodium sulfate. The solvent was distilled off to obtain crude product of N-ethoxycarbonyl-N-phenyl-7-amino-4,5,6,7-tetrahydrobenzo[b]thiophene-5,6-dicarboxylic acid dimethyl ester. Silica gel column chromatography using a developing solution of hexane/ethyl acetate=3/1, gave a fraction containing the desired product, which was concentrated by distilling off the solvent, to obtain 1.2 g (yield: 57.7% from imine) of N-ethoxycarbonyl-N-phenyl-7-amino-4,5,6,7-tetrahydrobenzo[b]thiophene-5,6-dicarboxylic acid dimethyl ester. $^1$H-NMR spectra (chemical shift, ppm: In $CDCl_3$): 0.90–1.30 (3H, m), 1.58–2.73 (joined 2H, m), 2.80–3.25 (2H, m), 3.50–3.80 (6H, m), 3.90–4.30 (2H, m), 5.10–6.30 (joined 1H, m), 6.60–6.95 (2H, m), 7.10–7.60 (5H, m).

The thus obtained N-ethoxycarbonyl-N-phenyl-7-amino-4,5,6,7-tetrahydrobenzo[b]thiophene-5,6-dicarboxylic acid dimethyl ester was dissolved in methanol (10 ml), to which sodium methoxide (1 g in 28% methanol solution) was added and stirred at room temperature for 2 hours. After adding water to the reaction mixture and distilling off methanol, water was added to the residue, which was extracted with ethyl acetate. The liquid extract was washed with an aqueous solution of sodium chloride and then dried over sodium sulfate. The solvent was distilled off and the residue submitted to silica gel column chromatography. Elution with a developing solvent of hexane/ethyl acetate= 3/1 gave a fraction containing the desired product, which was concentrated by distilling off the solvent, to obtain 0.6 g (yield: 47.5% from imine) of 4,5-dihydrobenzo[b] thiophene-5,6-dicarboxylic acid dimethyl ester. $^1$H-NMR spectra (chemical shift, ppm: in $CDCl_3$): 2.90–3.10 (1H, m), 3.40–3.58 (1H, m), 3.63 (3H, s), 3.83 (3H, m), 3.85–4.00 (1H, m), 6.85–6.98 (1H, d, J=4.9 Hz) , 7.27–7.40 (1H, d, J=4.9 Hz), 7.67 (1H, s).

Example 14

3-methylthiophene-2-aldehydimine (1 g, 5 mmol), acrylonitrile (1.35 g, 25 mmol) and diisopropyl ethyl amine (1.28 g, 10 mmol) were mixed in toluene (4 ml) and stirred at 80° C. Ethyl chloroformate (1.07 g, 10 mmol) was added to the mixture. After completing the addition, the reaction mixture was heated for one hour under reflux and then allowed to cool to room temperature. Water was added and the mixture extracted with toluene. The organic layer was washed with an aqueous solution of sodium chloride and then dried over sodium sulfate. The solvent was distilled off to obtain crude products of N-ethoxycarbonyl-N-phenyl-7-amino-4,5,6,7-tetrahydrobenzo[b]thiophene-6-nitrile. The resultant residue was purified by recrystallization (ethyl acetate/hexane) to obtain 0.65 g (yield: 40.0% from imine) of N-ethoxycarbonyl-N-phenyl-7-amino-4,5,6,7-tetrahydrobenzo[b]thiophene-6-nitrile. $^1$H-NMR spectra (chemical shift, ppm: in $CDCl_3$): 1.00–1.30 (4H, m), 1.60 (1H, s), 1.70–1.89 (1H, m), 2.31–2.60 (2H, m), 3.11–3.27 (1H, m), 4.00–4.36 (2H, m), 6.25 (1H, s), 6.62–6.75 (1H, m), 6.90–7.11 (2H, s), 7.12–7.38 (3H, m).

The thus obtained N-ethoxycarbonyl-N-phenyl-7-amino-4,5,6,7-tetrahydrobenzo[b]thiophene-6-nitrile (100 mg) was dissolved in methanol (10 ml), to which sodium methoxide (1 g in 28% methanol solution) was added and stirred at 60° C. for 2 hours. Water was then added to the reaction mixture and, after distilling off the methanol, water was added to the residue, which was extracted with ethyl acetate. The liquid extract was washed with an aqueous solution of sodium chloride and then dried over sodium sulfate. The solvent was distilled off and the residue submitted to silica gel column chromatography. Elution with a developing solvent of hexane/ethyl acetate=3/1 gave a fraction containing the desired product, which was concentrated by distilling off the solvent, to obtain 40 mg (yield: 32.0% from imine) of 4,5,-dihydrobenzo[b]thiophene-6-nitrile. $^1$H-NMR spectra (chemical shift, ppm: in $CDCl_3$): 2.49–2.70 (2H, m), 2.74–3.00 (2H, m), 6.80–6.95 (1H, m), 7.16 (1H, s), 7.27–7.41 (1H, m).

Example 15

3-methylthiophene-2-aldehydimine (1 g, 5 mmol), methyl vinyl ketone (1.75 g, 25 mmol) and diisopropyl ethyl amine (1.28 g, 10 mmol) were mixed in toluene (4 ml) and stirred at 80° C. Ethyl chloroformate (1.07 g, 10 mmol) was added to the mixture. After completing the addition, the reaction mixture was heated for one hour under reflux and then allowed to cool to room temperature. Water was added and the mixture was extracted with toluene and washed with an aqueous solution of sodium chloride and dried over sodium sulfate. The solvent was distilled off to obtain crude products of N-ethoxycarbonyl-N-phenyl-7-amino-4,5,6,7tetrahydrobenzo[b]thiophene-6-acetyl. The resultant residue was purified by recrystallization (ethyl acetate/hexane) to obtain 0.70 g (yield: 40% from imine) of N-ethoxycarbonyl-N-phenyl-7-amino-4,5,6,7-tetrahydrobenzo[b]thiophene-6-acetyl-$^1$H-NMR spectra (chemical shift, ppm: in $CDCl_3$): 0.85–1.35 (4H, m), 1.50–1.90 (2H, m), 2.05–2.60 (4H, m), 2.90–3.08 (1H, m), 3.95–4.28 (2H, m), 5.90–6.77 (joined 3H, m), 6.90–7.31 (joined 5H, m).

The thus obtained N-ethoxycarbonyl-N-phenyl-7-amino-4,5,6,7-tetrahydrobenzo[b]thiophene-6-acetyl (100 mg) was dissolved in methanol (10 ml), to which sodium methoxide (1 g in 28% methanol solution) was added and stirred at room temperature for one hour. Water was then added to the reaction mixture, methanol was distilled off. Water was then added to the residue, which was extracted with ethyl acetate. The liquid extract was washed with an aqueous solution of sodium chloride and dried over sodium sulfate. The solvent was distilled off and the residue was submitted to silica gel column chromatography. Elution with a developing solvent of hexane/ethyl acetate=10/1 gave a fraction containing the desired product which was concentrated by distilling off the solvent, to obtain 40 mg. (yield: 31.2% from imine) of 4,5-dihydrobenzo[b]thiophene-6-acetyl. $^1$H-NMR spectra (chemical shift, ppm: in $CDCl_3$): 2.31 (3H, m), 2.40–2.85 (joined 4H, m), 6.71 (1H, m), 6.75–6.89 (1H, m), 6.90–7.01 (1H, m).

Example 16

3-methylfuran-2-carboxaldehyde (10 g, 0.09 mol) was mixed with hexane (40 ml), to which aniline (9.6 ml, 0.11 mol) was added and stirred at room temperature for 30 minutes. The reaction mixture was concentrated by distilling off the solvent and then submitted to silica gel column chromatography. Elution with a developing solvent of hexane/ethyl acetate=20/1 gave a fraction containing the desired product which was concentrated by distilling off the solvent, to obtain 5.2 g (yield: 31%) of 3-methylfuran-2-carboxaldehyde imine. $^1$H-NMR spectra (chemical shift, ppm: in $CDCl_3$): 2.32 (3H, s), 6.63 (1H, d, J=4.9 Hz), 7.05–7.25 (3H), 7.26–7.40 (3H), 8.32 (1H, s).

3-methylfuran-2-carboxaldehyde imine (1.5 g, 8.15 mmol), methyl acrylate (3.5 g, 40.7 mmol) and diisopropyl ethyl amine (2.1 g, 16.3 mmol) were mixed in toluene (6 ml) and stirred at 80° C. Ethyl chloroformate (1.77 g, 16.3 mmol) was added to the mixture. After completing the addition, the reaction mixture was heated for one hour under reflux and allowed to cool to room temperature. Water was added and the mixture was extracted with toluene. The organic layer was washed with an aqueous solution of sodium chloride and dried over sodium sulfate. The solvent was distilled off to obtain crude products of N-ethoxycarbonyl-N-phenyl-7-amino-4,5,6,7-tetrahydrobenzo[b]furan-6-carboxylic acid methyl ester. Silica gel column chromatography using a developing solvent of hexane/ethyl acetate=5/1, gave a fraction containing the desired product, which was concentrated by distilling off the solvent, to obtain 1.2 g (yield: 43.0% from imine) of N-ethoxycarbonyl-N-phenyl-7-amino-4,5,6,7tetrahydrobenzo[b]furan-6-carboxylic acid methyl ester. $^1$H-NMR spectra (chemical shift, ppm: in $CDCl_3$): 1.00–1.40 (3H, m), 1.65–2.10 (2H, m), 2.15–3.05 (joined 2H, m), 3.74 (3H, s), 3.95–4.30 (3H, m), 5.75–6.20 (joined 1H, m), 6.50–6.95 (2H, m), 7.00–7.50 (5H, m).

The thus obtained N-ethoxycarbonyl-N-phenyl-7-amino-4,5,6,7-tetrahydrobenzo[b]furan-6-carboxylic acid methyl ester was dissolved in methanol (10 ml), to which sodium methoxide (1 g in 28% methanol solution) was added. After stirring at 60° C. for 2 hours, water was added to the reaction mixture and methanol was distilled off. Water was then added to the residue, which was extracted with ethyl acetate. After washing the liquid extract with an aqueous solution of sodium chloride, it was dried over sodium sulfate. The solvent was distilled off and the residue was submitted to silica gel column chromatography. Elution with a developing solution of hexane/ethyl acetate=9/1 gave a fraction containing the desired product, which was concentrated by distilling off the solvent, to obtain 0.5 g (yield: 34.7% from imine) of 4,5-dihydrobenzo[b]furan-6-carboxylic acid methyl ester. $^1$H-NMR spectra (chemical shift, ppm: in $CDCl_3$): 2.51–2.80 (4H, m), 3.78 (3H, s), 6.33 (1H, s), 7.31–7.42 (2H, m).

What is claimed as new and is desired to be secured by Letters Patent of the United States is:

1. A 1-amino-2-cyclohexene compound represented by the following formula (I):

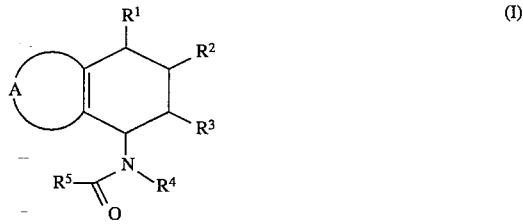

wherein A represents a bivalent organic group which may contain 1 to 3 oxygen atoms, nitrogen atoms and/or sulfur atoms, wherein A forms a ring having a total of 5–8 members, and the ring may form a condensed ring with one or more additional rings; $R^1$ represents a hydrogen atom, an alkyl group, an alkenyl group, an aryl group or an aralkyl group, $R^2$ represents a hydrogen atom, an alkyl group, an alkenyl group, an aryl group, an aralkyl group, a cyano group or a group represented by the formula: $-COR^{21}$, where $R^{21}$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, $R^3$ represents a cyano group, a nitro group or a group represented by the formula: —COR$^{31}$, where R$^{31}$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, R$^4$ represents an alkyl group, an alkenyl group, an aryl group or an aralkyl group, R$^5$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, in which R$^2$ and R$^{31}$ may join together to form a bivalent organic group optionally containing an oxygen atom or a nitrogen atom.

2. The 1-amino-2-cyclohexene compound as defined in claim 1, wherein the ring formed by A is a thiophene ring.

3. The 1-amino-2-cyclohexene compound as defined in claim 1, wherein the ring formed by A is an indole ring.

4. The 1-amino-2-cyclohexene compound as defined in claim 1, wherein the ring formed by A is a furan ring.

5. The 1-amino-2-cyclohexene compound as defined in claim 1, wherein R$^5$ is an alkoxy group, an aryloxy group or an aralkyloxy group.

6. The 1-amino-2-cyclohexene compound as defined in claim 1, wherein R$^3$ represents a group represented by the formula: —COR$^{31}$, and R$^{31}$ represents an alkoxy group, an aryloxy group or an aralkyloxy group.

7. A tetrahydrobenzothiophene or tetrahydrobenzofuran compound represented by the following formula (I-1):

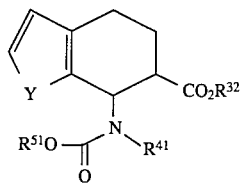

wherein each of R$^{32}$, R$^{41}$ and R$^{51}$ and R, independently, represents an alkyl group, an aryl group or an aralkyl group and Y represents a sulfur atom or an oxygen atom.

8. A tetrahydrobenzothiophene compound as defined in claim 7, wherein Y represents a sulfur atom.

9. A tetrahydrocarbazole compound represented by the following formula (I-2):

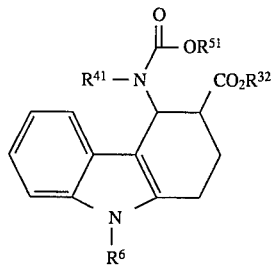

wherein each of R$^{32}$, R$^{41}$ and R$^{51}$, independently represents an alkyl group, an aryl group or an aralkyl group, and R$^6$ represents an alkyl group, an aralkyl group, an acyl group, an alkoxycarbonyl group, an alkane sulfonyl group or an arene sulfonyl group.

10. A process for producing a 1-amino-2-cyclohexene compound represented by the following formula (I):

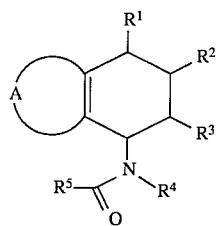

wherein A represents a bivalent organic group which may contain 1 to 3 oxygen atoms, nitrogen atoms and/or sulfur atoms, wherein A forms a ring having a total of 5–8 members, and the ring may form a condensed ring with one or more additional rings; R$^1$ represents a hydrogen atom, an alkyl group, an alkenyl group, an aryl group or an aralkyl group, R$^2$ represents a hydrogen atom, an alkyl group, an alkenyl group, an aryl group, an aralkyl group, a cyano group or a group represented by the formula: —COR$^{21}$, where R$^{21}$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, R$^3$ represents a cyano group, a nitro group or a group represented by the formula: —COR$^{31}$, where R$^{31}$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, R$^4$ represents an alkyl group, an alkenyl group, an aryl group or an aralkyl group, R$^5$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, in which R$^2$ and R$^{31}$ may join together to form a bivalent organic group optionally containing an oxygen atom or a nitrogen atom, which comprises condensing an aldehyde represented by the formula (II):

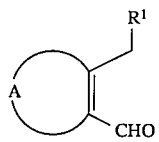

where A and R$^1$ are as defined above, with a primary amine represented by the following formula (III):

H$_2$NR$^4$     (III)

where R$^4$ is as defined above, to obtain an imine represented by the following formula (IV):

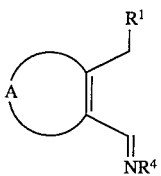

where A, R$^1$ and R$^4$ are as defined above; and reacting the imine (IV) in the presence of a basic substance, with a carbonylating agent represented by the following formula (V):

   (V)

where $R^5$ is as defined above and X represents a leaving group and an ethylene compound represented by the following formula (VI):

   (VI)

where $R^2$ and $R^3$ are as defined above.

11. A process for producing a 1-amino-2-cyclohexene compound as defined in claim 10, wherein the ring formed by A is a thiophene ring.

12. A process for producing a 1-amino-2-cyclohexene compound as defined in claim 10, wherein the ring formed by A is an indole ring.

13. A process for producing a 1-amino-2-cyclohexene compound as defined in claim 10, wherein the ring formed by A is a furan ring.

14. A process for producing a 1-amino-2-cyclohexene compound as defined in claim 10, wherein the carbonylating agent is chloroformate ester.

15. A process for producing a 1-amino-2-cyclohexene compound as defined in claim 10, wherein the ethylene compound is an acrylate ester.

16. A process for producing a 1-amino-2-cyclohexene compound as defined in claim 10, wherein the aldehyde is 3-methylthiophene-2-aldehyde or 3-methylfuran-2-aldehyde represented by the following formula (VII):

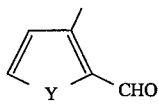   (VII)

where Y represents a sulfur atom or an oxygen atom.

17. A process for producing a 1-amino-2-cyclohexene compound as defined in claim 16, wherein Y represents a sulfur atom.

18. A process for producing a 1-amino-2-cyclohexene compound as defined in claim 10, wherein the aldehyde is 2-methylindole-3-aldehyde represented by the following formula (VIII):

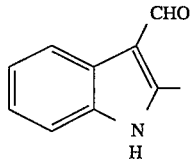   (VIII)

19. A process for producing a 1,3-cyclohexadiene compound represented by the following formula (IX):

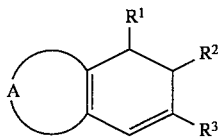   (IX)

wherein A represents a bivalent organic group which may contain 1 to 3 oxygen atoms, nitrogen atoms and/or sulfur atoms, wherein A forms a ring having a total of 5–8 members, and the ring may form a condensed ring with one or more additional rings; $R^1$ represents a hydrogen atom, an alkyl group, an alkenyl group, an aryl group or an aralkyl group, $R^2$ represents a hydrogen atom, an alkyl group, an alkenyl group, an aryl group, an aralkyl group, a cyano group or a group represented, by the formula: $-COR^{21}$, wherein $R^{21}$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, and $R^3$ represents a cyano group, a nitro group or a group represented by the formula: $-COR^{31}$, wherein $R^{31}$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, in which $R^2$ and $R^{31}$ may join together to form a bivalent organic group optionally containing an oxygen atom or a nitrogen atom, which comprises subjecting a 1-amino-2-cyclohexene compound represented by the following formula (I):

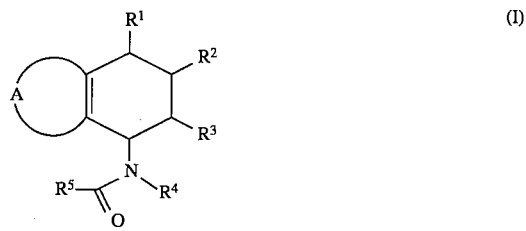   (I)

where A, $R^1$, $R^2$ and $R^3$ are as defined above, $R^4$ represents an alkyl group, an alkenyl group, an aryl group or an aralkyl group, and $R^5$ represents a hydrogen atom, an alkyl group, an alkenyl group, an aryl group, an aralkyl group, an alkoxy group, an alkenyloxy group, an aryloxy group, an aralkyloxy group or an amino group which may have a substituent, to an elimination reaction by a basic substance.

20. A process for producing a 1,3-cyclohexadiene compound as defined in claim 19, wherein the ring formed by A is a thiophene ring.

21. A process for producing a 1,3-cyclohexadiene compound as defined in claim 19, wherein the ring formed by A is an indole ring.

22. A process for producing a 1,3-cyclohexadiene compound as defined in claim 19, wherein the ring formed by A is a furan ring.

23. A process for producing a dihydrobenzothiophene carboxylic acid or dihydrobenzofuran carboxylic acid compound represented by the following formula (IX-1):

   (IX-1)

where Y represents a sulfur atom or oxygen atom and $R^{33}$ represents a hydrogen atom, an alkyl group, aryl group, or aralkyl group, in which a tetrahydrobenzothiophene or tetrahydrobenzofuran compound represented by the following formula (I-1):

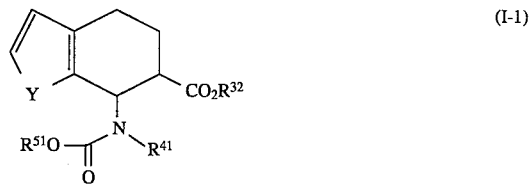   (I-1)

where each of $R^{32}$, $R^{41}$ and $R^{51}$ represents an alkyl group or an aralkyl group and Y is as defined above, is subjected to an elimination reaction with a basic substance and, optionally, to hydrolysis.

24. The process for producing a dihydrobenzothiophene carboxylic acid compound as defined in claim 23, wherein Y represents a sulfur atom.

25. A process for producing a dihydrocarbazole carboxylic acid compound represented by the following formula (X-2):

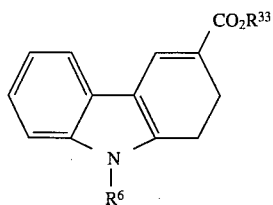
(IX-2)

where $R^{33}$ represents a hydrogen atom, an alkyl group, aryl group or aralkyl group and $R^6$ represents an alkyl group, aralkyl group, acyl group, alkoxycarbonyl group, alkane sulfonyl group or arene sulfonyl group, comprising subjecting a tetrahydrocarbazole compound represented by the following formula (I-2):

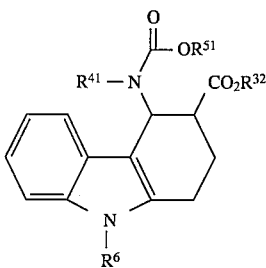
(I-2)

where each of $R^{32}$, and $R^{41}$ and $R^{51}$ represents an alkyl group an aryl group, or an aralkyl group and $R^6$ is as defined above, to an elimination reaction with a basic substance and, optionally, to hydrolysis.

\* \* \* \* \*